United States Patent [19]

Orr et al.

[11] 4,232,012

[45] Nov. 4, 1980

[54] COMPOSITION

[75] Inventors: Thomas S. C. Orr, Melton Mowbray; David E. Hall, Burton-on-the-Wolds; John Mann, Long Whatton, all of England

[73] Assignee: Fisons Limited, London, England

[21] Appl. No.: 12,327

[22] Filed: Feb. 15, 1979

Related U.S. Application Data

[60] Division of Ser. No. 863,859, Dec. 23, 1977, Pat. No. 4,151,292, which is a continuation-in-part of Ser. No. 742,750, Nov. 18, 1976, Pat. No. 4,066,756.

[30] Foreign Application Priority Data

Jan. 25, 1977 [GB] United Kingdom ................. 2872/77

[51] Int. Cl.$^2$ ........................................... A61K 31/625
[52] U.S. Cl. ................................................... 424/232
[58] Field of Search ......................................... 424/232

[56] References Cited

U.S. PATENT DOCUMENTS 3,419,578   12/1968   Fitzmaurice et al. ................. 424/278

OTHER PUBLICATIONS

Chem. Abst. 57-7866i (1972).

*Primary Examiner*—Stanley J. Friedman
*Attorney, Agent, or Firm*—Merriam, Marshall & Bicknell

[57] ABSTRACT

There is described a pharmaceutical composition comprising one or more of 1,3-bis(2-carboxychromon-5-yloxy)propan-2-ol; 5-(2-hydroxy-propoxy)-8-propyl-chromone-2-carboxylic acid; 6,7,8,9-tetrahydro-4-oxo-10-propyl-4H-naphtho[2,3-b]pyran-2-carboxylic acid; 6,7,8,9-tetrahydro-5-hydroxy-4-oxo-10-propyl-4H-naphtho[2,3-b]pyran-2-carboxylic acid; or a pharmaceutically acceptable salt of any one thereof, in combination with one or more of aspirin, indomethacin, phenylbutazone or oxyphenbutazone. (Mixtures of 1,3-bis(2-carboxychromon-5-yloxy)propan-2-ol, or a pharmaceutically acceptable salt thereof, with aspirin or indomethacin do not form part of the invention).

There are also described packages containing the separate components of the composition and pharmaceutical formulations containing the composition.

14 Claims, No Drawings

COMPOSITION

This is a division of application Ser. No. 863,859, filed Dec. 23, 1977, now U.S. Pat. No. 4,151,292, which latter application is in turn a continuation-in-part of application Ser. No. 742,750, filed Nov. 18, 1976, now U.S. Pat. No. 4,066,756.

This invention relates to a mixture and a method for its preparation.

Aspirin, indomethacin, phenylbutazone, oxyphenbutazone and mixtures thereof (herein referred to collectively as 'the anti-inflammatory'), are widely used in the treatment of inflammatory conditions, but suffer from the disadvantage that they can cause gastro-intestinal irritation, pain, nausea, indigestion and in particular gastro-intestinal micro bleeding. We have now surprisingly found that the gastro-intestinal side effects of the anti-inflammatory can be inhibited by the application of certain chromone compounds in combination with the anti-inflammatory.

According to our invention therefore we provide a pharmaceutical composition comprising one or more of 1,3-bis(2-carboxychromon-5-yloxy)propan-2-ol; 5-(2-hydroxypropoxy)-8-propylchromone-2-carboxylic acid; 6,7,8,9-tetrahydro-4-oxo-10-propyl-4H-naphtho[2,3-b]pyran-2-carboxylic acid; 6,7,8,9-tetrahydro-5-hydroxy-4-oxo-10-propyl-4H-naphtho[2,3-b]pyran-2-carboxylic acid; or a pharmaceutically acceptable salt of any one thereof, (herein referred to collectively as 'active ingredient') in combination with the anti-inflammatory, provided that the composition does not comprise 1,3-bis(2-carboxychromon-5-yloxy)propan-2-ol, or a pharmaceutically acceptable salt thereof, in combination with aspirin or indomethacin.

We prefer to use the di-sodium salt of 1,3-bis(2-carboxychromon-5-yloxy)propan-2-ol, which is commonly known as disodium cromoglycate, or cromolyn sodium.

We prefer the mixture to contain only one active ingredient and only one anti-inflammatory.

The ratios of anti-inflammatory to one part by weight of active ingredient (calculated as the mono-sodium salt or, in the case of 1,3-bis(2-carboxychromon-5-yloxy)propan-2-ol, as the di-sodium salt) are as follows:

| Anti-inflammatory (parts by weight) | Active Ingredient (one part by weight) |
|---|---|
| (a) Phenylbutazone or oxyphenbutazone | |
| 2,000 to 0.14 preferably 200 to 0.35 more preferably 200 to 1.4 | 1,3-bis-(2-carboxychromon-5-yloxy)propan-2-ol or a pharmaceutically acceptable salt thereof |
| (b) Aspirin | |
| 24 to 0.024 preferably 4.0 to 0.12 | 5-(2-hydroxypropoxy)-8-propyl-chromone-2-carboxylic acid, or a pharmaceutically acceptable salt thereof |
| (c) Indomethacin | |
| 4.0 to 0.004 preferably 4.0 to 0.01 | 5-(2-hydroxypropoxy -8-propyl-chromone-2-carboxylic acid, or a pharmaceutically acceptable salt thereof |
| (d) Phenylbutazone or oxyphenbutazone | |
| 8.0 to 0.028 preferably 8.0 to 0.14 | 5-(2-hydroxypropyl)-8-propyl-chromone-2-carboxylic acid, or a pharmaceutically acceptable salt thereof |
| (e) Aspirin | |
| 1200 to 0.3 preferably 1200 to 0.6 | 6,7,8,9-tetrahydro-4-oxo-10-propyl-4H-naphtho[2,3-b]-pyran-2-carboxylic acid, or 6,7,8,9-tetrahydro-5-hydroxy-4-oxo-10-propyl-4H-naphtho[2,3-b]pyran-2-carboxylic acid or a pharmaceutically acceptable salt of either thereof |
| (f) Indomethacin | |
| 200 to 0.05 preferably 200 to 0.1 | 6,7,8,9-tetrahydro-4-oxo-10-propyl-4H-naphtho [2,3-b,]-pyran-2-carboxylic acid, or 6,7,8,9-tetrahydro-5-hydroxy-4-oxo-10-propyl-4H-naphtho[2,3-b]pyran-2-carboxylic acid or a pharmaceutically acceptable salt of either thereof |
| (g) Phenylbutazone or oxyphenbutazone | |
| 400 to 0.35 preferably 400 to 0.7 | 6,7,8,9-tetrahydro-4-oxo-10-propyl-4H-naphtho[2,3-b]-pyran-2-carboxylic acid, or 6,7,8,9-tetrahydro-5-hydroxy-4-oxo-10-propyl-4H-naphtho[2,3-b-]pyran-2-carboxylic acid or a pharmaceutically acceptable salt of either thereof |

The daily dosages for humans for most anti-inflammatory purposes of the anti-inflammatories are as follows:

(a) Aspirin 3 to 80, and preferably 3 to 40, mg/kg of the subject to be treated's body weight.

For an adult human 180 mg to 4.8 g, preferably 180 mg to 2.4 g, preferably given in divided doses 3 to 8, and preferably 3 to 4 times a day.

(b) Indomethacin 0.33 to 8.33, and preferably 0.83 to 2.5, mg/kg of the subject to be treated's body weight.

For an adult human 20 to 500, preferably 50 to 150 mg, preferably given in divided doses 2 to 5 and preferably 2 to 3 times per day.

(c) Phenylbutazone or Oxyphenbutazone 1.7 to 15, and preferably 3.3 to 10, mg/kg of the subject to be treated's body weight.

For an adult human 100 to 900, preferably 200 to 600, mg preferably given in divided doses 2 to 3 times per day.

Each dose of the anti-inflammatory may comprise one or more unit doses, e.g. tablets or capsules.

The daily dosages of the active ingredient can, if desired, be obtained by simple calculation.

For human use compositions in unit dosage form comprise the quantities of active ingredient (calculated as the mono-sodium salt and, in the case of 1,3-bis(2-carboxychromon-5-yloxy)propan-2-ol, as the di-sodium salt), and of the anti-inflammatory specified below:

(a) Aspirin 60 to 600 mg, preferably 180 to 600 mg.
(b) Indomethacin 10 to 100 mg, preferably 25 to 50 mg.
(c) Phenylbutazone or oxyphenbutazone 70 to 200 mg, preferably 100 to 200 mg.
(d) 1,3-Bis-(2-carboxychromon-5-yloxy)propan-2-ol
   0.1 to 500 mg, preferably 1 to 200 mg and more preferably 1 to 50 mg.
(e) 5-(2-Hydroxypropoxy)-8-propyl-chromone-2-carboxylic acid
   25 mg to 2.5 g, preferably 25 to 500 mg.
(f) 6,7,8,9-Tetrahydro-4-oxo-10-propyl-4H-naphtho[2,3-b]pyran-2-carboxylic acid or 6,7,8,9-tetrahydro-5-hydroxy-4-oxo-10-propyl-4H-naphtho-[2,3-b]pyran-2-carboxylic acid
   0.5 to 200 mg, preferably 0.5 to 100 mg.

According to our invention we also provide a method for the treatment of an inflammatory and/or painful condition, e.g. arthritis such as rheumatoid arthritis, rheumatism and other disorders, e.g. inflammatory disorders or platelet aggregation, normally treated with the anti-inflammatory, which comprises administration of a composition according to the invention to an individual mammal, e.g. human, suffering from such a condition. The administration is preferably per os, and is most preferably administration by mouth (oesophageal administration).

According to the invention we also provide a method for the treatment of an inflammatory and/or painful condition, e.g. arthritis such as rheumatoid arthritis, rheumatism, and other disorders, e.g. inflammatory disorders or platelet aggregation, normally treated with the anti-inflammatory, which comprises sequential or simultaneous administration of active ingredient and the anti-inflammatory (provided that the administration does not comprise administration of 1,3-bis(2-carboxychromon-5-yloxy)-propan-2-ol, or a pharmaceutically acceptable salt thereof, and aspirin or indomethacin) to an individual mammal, e.g. human, suffering from such a condition or disorder.

The active ingredient is preferably administered in such a way that it is available in the gastrointestinal tract before the anti-inflammatory, e.g. the active ingredient may be administered before the anti-inflammatory. Alternatively the active ingredient may be administered together with, or after the anti-inflammatory, but in such circumstances the anti-inflammatory is preferably used in delayed or sustained release form.

When sequential or simultaneous administration of active ingredient and the anti-inflammatory is used the ratios and dosages of the active ingredient and the anti-inflammatory are as described above with respect to the mixtures.

The invention therefore also provides a pharmaceutical package comprising at least one unit dose of active ingredient and at least one unit dose of the anti-inflammatory, provided that the package does not comprise a unit dose of 1,3-bis(2-carboxychromon-5-yloxy)-propan-2-ol, or a pharmaceutically acceptable salt thereof, and a unit dose of aspirin or indomethacin. The unit doses are preferably arranged in the package in a particular order together with written or printed indications or directions, the indications or directions and the manner of packing being such as to provide guidance in relation to and to facilitate the taking of a unit dose of active ingredient and a unit dose of the anti-inflammatory in a particular order, e.g. a unit dose of the former before a unit dose of the latter. The package is preferably a sealed package and may comprise a tube, box or chart in or on which the unit doses are packed. The unit doses are preferably suitable for oesophageal administration and preferably contain the doses of active ingredient and the anti-inflammatory in the ratios set out above for the combinations.

The suppression of the side effects of the anti-inflammatory may be further enhanced by the post- or preferably pre-dosing of the subject with additional active ingredient.

In order to produce suitable compositions the active ingredient and the anti-inflammatory, either separately or as a mixture thereof, may be mixed with organic or inorganic pharmaceutically acceptable adjuvants, diluents or excipients. Examples of such adjuvants are:

For tablets and dragées: Binders, for example, cellulosic materials, e.g. microcrystalline cellulose and methyl cellulose; disintegrating agents, for example starches, e.g. maize starch; stabilizers, e.g. against hydrolysis of the active ingredients; flavouring agents, for example sugars such as lactose; fillers; stearates and inorganic diluents, e.g. talc.

For syrups, suspensions or dispersions: A liquid vehicle in which the active ingredients may be dissolved or suspended, e.g. water; and suspending agents, e.g. cellulose derivatives, gums etc.

For hard or soft capsules: Diluents, e.g. lactose; glidants, e.g. stearates; inorganic materials, e.g. silica or talc; stabilizers and dispersing agents.

For suppositories: Natural or hardened oils, waxes etc. A large number of proprietary emulsifying bases are available and are suitable for use in suppositories. These include 'Witepsol' bases, consisting of hydrogenated triglycerides of lauric acid with added monoglycerides; and 'Massupol' bases, which consist of glyceryl esters of lauric acid with a very small amount of glyceryl monostearate.

For enemas: Water, sodium chloride, buffers etc.

We prefer compositions which are designed to be administered by mouth (oesophageally).

The composition may also contain further adjuvants, for example a composition for use in tablets may contain lubricants and glidants to assist in tabletting, e.g. magnesium stearate, or wetting agents to assist in granulation, e.g. dioctyl sodium sulphosuccinate. The composition may also if desired contain a pharmaceutically acceptable dye or colourant, and may, if desired, be coated using conventional film or sugar coating techniques.

If desired the composition, or one or more components thereof, may be formulated in sustained release form, e.g. by coating some or all of the drug particles themselves or granules thereof made with, for example, sucrose and of a size up to 2 mm in diameter with a layer of, e.g. beeswax, Carnuba wax, stearic or palmitic acids, cetyl alcohol or similar substances which could be expected to be slowly dissolved or digested or to act as semi-permeable membranes through which the drugs can diffuse when the preparations are ingested. The composition may contain drug particles or granules which are uncoated in admixture with particles or granules having one or more coats of the coating medium, and may be in the form of a capsule containing the particles or granules or alternatively a tablet, for which other adjuvants may be required, such as glidants or lubricants. The mixture may be administered as an enteric coated composition to make the drugs available at the appropriate part of the gastro-intestinal tract. This may be achieved by coating the tablet with a continuous film of material which is resistant and impermeable to gastric secretions, but which is susceptible to intestinal secretions. Typical film materials are shellac and its derivatives and cellulose acetate phthalate.

We prefer compositions which are adapted to release some or all of the active ingredient first and to release the anti-inflammatory later. Thus a solid composition may comprise a core of the anti-inflammatory surrounded in part or in whole by an outer layer containing the active ingredient. The core may, if desired or necessary, be coated with a material which is relatively slowly dissolved or degraded by the gastric juices, e.g. shellac, beeswax, Carnuba wax, stearic or palmitic acids, or cetyl alcohol or the like and this coating may in turn be coated with a material containing the active ingredient which is relatively quickly dissolved or degraded by the gastric juices, e.g. sugar or a cellulose ether such as hydroxypropylmethylcellulose. Alternatively the composition may comprise discrete particles of the active ingredient, which may be coated or uncoated, but which are adapted to dissolve or disperse quickly in the gastro-intestinal tract, in admixture with discrete particles of the anti-inflammatory which are preferably coated or treated so that they dissolve or disperse the anti-inflammatory slowly in the gastrointestinal tract. We prefer the composition to be such that the anti-inflammatory begins to be available in the gastrointestinal tract from about 5 to 15 minutes after the active ingredient commences to be available in the gastrointestinal tract.

The active ingredient and the anti-inflammatory may, if desired, be used in a specific form, e.g. having a mass median diameter of less than 10 microns.

The active ingredient and the anti-inflammatory may also be formulated as an aqueous, e.g. a water chloroform (400:1), solution containing from 0.001 to 10.0% by weight of the active ingredient plus the anti-inflammatory.

We prefer compositions containing aspirin.

The compositions according to the invention may be made by, e.g. dry mixing the active ingredient and the anti-inflammatory optionally together with a pharmaceutically acceptable adjuvant, diluent or excipient, for example in a powder blending machine. The mixing may be carried out in two stages, the blend, or parts thereof, being sieved through an appropriate screen (e.g. 60 mesh, 250 micron) at the end of a first stage in order to disperse any persistant aggregates. The sieved powder may then be mixed further. The resulting mixture may then, for example, be compressed in a tablet forming machine or filled into a capsule.

We also provide a process for the production of unit dosage forms according to the invention, which comprises forming a mixture of the active ingredient and the anti-inflammatory, optionally in admixture with a pharmaceutically acceptable adjuvant, diluent or carrier, into discreet and separate units each of which comprises the required unit dosage. The forming into discreet units will normally be effected by filling an appropriate volume (or weight) of the finely divided or granulated active ingredient and anti-inflammatory, optionally in combination with an adjuvant, diluent or carrier into a defined space, e.g. a capsule, or the die of a tabletting machine.

The invention is illustrated, but in no way limited by the following Examples.

EXAMPLE 1

|  | mg/tablet |
| --- | --- |
| Phenylbutazone or oxyphenbutazone | 100 |
| Disodium cromoglycate | 100 |
| Maize starch BP as binder | 15 |
| Maize starch BP as disintegrant | 45 |
| Microcrystalline cellulose BPC | 80 |
| Talc | 10 |
|  | 350 |

EXAMPLE 2

1. Central Core Formulation

Phenylbutazene or oxyphenbutazone 100 mg
Maize Starch BP 45 mg

Sieve the phenylbutazone or oxyphenbutazone through a 20 mesh sieve and the maize starch through a 40 mesh sieve. Mix these ingredients and compress into 'slugs'. Granulate the 'slugs' using a 12 mesh screen.

2. Formulation of Outer Layer

|  | mg | % By weight |
| --- | --- | --- |
| 1,3-Bis(2-carboxychromon-5-yloxy)-2-hydroxypropane, disodium salt | 100 | 49.8 |
| Sodium bicarbonate BP | 75 | 37.3 |
| Maize starch BP | 17.8 | 8.9 |
| Talc BP (sterilised) | 8.0 | 4.0 |
| Purified water BP | QS | QS |
|  | 200.8 | 100.0 |

The sodium bicarbonate, after being passed through a 100 mesh screen, was mixed in a drum roller with the bis-chromone, which had been passed through a 60 mesh screen. Half the starch was then added, and the drum was rolled for about 20 minutes. The mixed powder was then transferred to a mixing bowl and dampened down with the water (approximately 120 ml per kg of dry powder). The damped powder was then passed through an 8 mesh screen and was dried at 50° C. for 2 hours, the dry product then being passed through a 16 mesh screen and blended with the talc and the remaining starch.

3. Intermediate Layer

An inert intermediate layer may, if desired, be used between the core and outer layer to delay the onset of disintegration and dissolution of the phenylbutazone or oxyphenbutazone containing core. This intermediate layer may consist of fillers, e.g. lactose, dicalcium phosphate, a polymeric binder e.g. gelatin, polyvinylpyrrolidone, and a lubricant e.g. metallic stearates, talc etc. A suitable formulation comprises:

Lactose BP 120 mg
Dicalcium phosphate USP XVII 30 mg
Gelatin BP 3 mg
Magnesium stearate BP 1 mg The lactose and dicalcium phosphate, after being passed through a 40 mesh sieve, were mixed in a planetary mixer for 10 minutes and damped down with a 12% w/w aqueous solution of the gelatin (approx 150 ml solution per kg of dry powder). The damped down mixture was then passed through an 8 mesh screen and dried at 60° C. for 2 hours, the dry product then being passed through a 20 mesh screen and blended with the magnesium stearate.

Compression

The core formulation may be compressed into a solid core and the intermediate and outer layers may be compressed around this core using a suitable rotary compression coating machine, e.g. a 'Manesty', 'Drycota' or 'Bicota' machine.

We claim:

1. A pharmaceutical composition adapted for oesophageal administration to a mammal comprising, as active ingredient, at least one chromone compound selected from 5-(2-hydroxypropoxy)-8-propyl-chromone-2-carboxylic acid; 6,7,8,9-tetrahydro-4-oxo-10-propyl-4H-naphtho-[2,3,-b]-pyran-2-carboxylic acid; 6,7,8,9-tetrahydro-5-hydroxy-4-oxo-10-propyl-4H-naphtho[2,3,-b]pyran-2-carboxylic acid or a pharmaceutically acceptable salt of any one thereof, in combination with an anti-inflammatory selected from aspirin, indomethacin, and mixtures thereof, said composition containing 0.004 to 1200 parts by weight of said anti-inflammatory per part of said active ingredient.

2. A composition according to claim 1, comprising from 24 to 0.024 parts of aspirin for each part by weight (calculated as the sodium salt) of 5-(2-hydroxypropoxy)-8-propyl-chromone-2-carboxylic acid, or a pharmaceutically acceptable salt thereof.

3. A composition according to claim 1, comprising from 4.0 to 0.004 parts by weight of indomethacin for each part by weight (calculated as the sodium salt) of 5-(2-hydroxypropoxy)-8-propyl-chromone-2-carboxylic acid, or a pharmaceutically acceptable salt thereof.

4. A composition according to claim 1, comprising from 1200 to 0.3 parts by weight of aspirin for each part by weight (calculated as the sodium salt) of 6,7,8,9-tetrahydro-4-oxo-10-propyl-4H-naphtho[2,3-b]pyran-2-carboxylic acid, or 6,7,8,9-tetrahydro-5-hydroxy-4-oxo-10-propyl-4H-naphtho[2,3-b]-pyran-2-carboxylic acid, or a pharmaceutically acceptable salt of either thereof.

5. A composition according to claim 1, comprising from 200 to 0.05 parts by weight of indomethacin for each part by weight (calculated as the sodium salt) of 6,7,8,9-tetrahydro-4-oxo-10-propyl-4H-naphtho[2,3-b]pyran-2-carboxylic acid, or 6,7,8,9-tetrahydro-5-hydroxy-4-oxo-10-propyl-4H-naphtho[2,3-b]-pyran-2-carboxylic acid, or a pharmaceutically acceptable salt of either thereof.

6. A composition according to claim 1 comprising from 60 to 600 mg of aspirin in unit dosage form.

7. A composition according to claim 1, comprising from 10 to 100 mg of indomethacin in unit dosage form.

8. A composition according to claim 1, comprising from 25 mg to 2.5 g of 5-(2-hydroxypropoxy)-8-propyl-chromone-2-carboxylic acid, or of a pharmaceutically acceptable salt thereof, calculated as the sodium salt, in unit dosage form.

9. A composition according to claim 1, comprising from 0.5 to 200 mg of 6,7,8,9-tetrahydro-4-oxo-10-propyl-4H-naphtho-[2,3-b]-pyran-2-carboxylic acid, of 6,7,8,9-tetrahydro-5-hydroxy-4-oxo-10-propyl-4H-naphtho[2,3-b]-pyran-2-carboxylic acid, or a pharmaceutically acceptable salt of either thereof, calculated as the sodium salt, in unit dosage form.

10. A composition according to claim 1 adapted to release some or all of the active ingredient first and to release the anti-inflammatory later.

11. A package according to claim 1, wherein the unit doses are arranged in an order which facilitates the administration to a mammal of a unit dose of active ingredient prior to or simultaneously with a unit dose of the anti-inflammatory.

12. A pharmaceutical package comprising at least one unit dose of the active ingredient of claim 1 and at least one unit dose of the anti-inflammatory of claim 1.

13. A method of administering an anti-inflammatory to a mammal with inhibition of adverse gastrointestinal effects due to said anti-inflammatory which method comprises orally administering to said mammal a composition according to claim 1.

14. A method of inhibiting adverse gastrointestinal effects created in a mammal by administration of an anti-inflammatory in accordance with claim 1, which method comprises administering to said mammal an active ingredient in accordance with claim 1, in the proportion of 0.004 to 1200 parts by weight of anti-inflammatory per part of active ingredient, said active ingredient being administered sequentially or substantially simultaneously with the administration of said anti-inflammatory.

* * * * *

UNITED STATES PATENT AND TRADEMARK OFFICE
CERTIFICATE OF CORRECTION

PATENT NO. : 4,232,012
DATED : November 4, 1980
INVENTOR(S) : THOMAS S. C. ORR ET AL.

It is certified that error appears in the above-identified patent and that said Letters Patent are hereby corrected as shown below:

Col. 1, line 65, "hydroxypropyl", should be --hydroxypropoxy--.

Col. 6, line 16, "Phenylbutazene", should be --Phenylbutazone--.

Signed and Sealed this

Twenty-fourth Day of February 1981

[SEAL]

Attest:

RENE D. TEGTMEYER

Attesting Officer

Acting Commissioner of Patents and Trademarks